US007648695B2

(12) United States Patent
Dees et al.

(10) Patent No.: US 7,648,695 B2
(45) Date of Patent: *Jan. 19, 2010

(54) MEDICAMENTS FOR CHEMOTHERAPEUTIC TREATMENT OF DISEASE

(75) Inventors: H. Craig Dees, Knoxville, TN (US); Timothy C. Scott, Knoxville, TN (US)

(73) Assignee: Provectus Pharmatech, Inc., Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/900,355

(22) Filed: Jul. 6, 2001

(65) Prior Publication Data

US 2002/0161035 A1  Oct. 31, 2002

Related U.S. Application Data

(63) Continuation-in-part of application No. 09/130,041, filed on Aug. 6, 1998, now abandoned, and a continuation-in-part of application No. 09/635,276, filed on Aug. 9, 2000, now abandoned, which is a continuation-in-part of application No. 09/216,787, filed on Dec. 21, 1998, now Pat. No. 6,331,286, and a continuation-in-part of application No. 09/799,785, filed on Mar. 6, 2001, now Pat. No. 7,390,668.

(60) Provisional application No. 60/218,464, filed on Jul. 14, 2000.

(51) Int. Cl.
A61K 51/00 (2006.01)
A61M 36/14 (2006.01)
G01N 33/00 (2006.01)

(52) U.S. Cl. .............. 424/9.37; 424/1.11; 424/1.13; 424/1.17; 424/1.33; 436/125

(58) Field of Classification Search .............. 424/178.1; 514/44, 2, 454; 609/20
See application file for complete search history.

(56) References Cited

U.S. PATENT DOCUMENTS

| 3,563,750 | A | * | 2/1971 | Walker ........................ 430/332 |
| 4,490,543 | A | | 12/1984 | Berquist et al. |
| 4,647,578 | A | | 3/1987 | Crounse et al. |
| 4,846,789 | A | * | 7/1989 | Heitz et al. .................. 604/522 |
| 4,867,973 | A | * | 9/1989 | Goers et al. .............. 424/181.1 |
| 5,162,218 | A | * | 11/1992 | Schultz ........................ 435/188 |
| 5,576,013 | A | * | 11/1996 | Williams et al. ............. 424/423 |
| 5,780,052 | A | | 7/1998 | Khaw et al. |
| 6,331,286 | B1 | * | 12/2001 | Dees et al. .................. 424/1.85 |
| 6,991,776 | B2 | | 1/2006 | Dees et al. |
| 7,384,623 | B1 | * | 6/2008 | Dees et al. .................. 424/9.37 |
| 7,390,668 | B2 | * | 6/2008 | Dees et al. .................. 436/124 |

FOREIGN PATENT DOCUMENTS

| EP | 0 175 617 A | 3/1986 |
| WO | WO 96/07431 | 3/1996 |
| WO | WO 97/03697 | 2/1997 |
| WO | WO 9703697 A2 * | 2/1997 |
| WO | WO 97/26920 | 7/1997 |
| WO | WO 97/39064 | 10/1997 |
| WO | WO 9739064 A1 * | 10/1997 |
| WO | WO 00/25665 | 5/2000 |
| WO | WO 00/37927 | 6/2000 |
| WO | WO 01/72301 A1 | 10/2001 |
| WO | WO 01/76595 A1 | 10/2001 |

OTHER PUBLICATIONS

Shi et al. J. Org. Chem. 1992,57, 4418-4421.*
Search report re: PCT/US01/21585. Dated Oct. 18, 2001.
International Preliminary Examination Report regarding application No. PCT/US01/21585, mailed Sep. 19, 2002.
American Cancer Society, "What is Chemotherapy?" page from website, http://www.cancer.org/docroot/ETO/eto_1_3_Chemotherapy_Principles.asp;printed Sep. 11, 2003.
WebMD.com, "Chemotherapy," page from website, http://my.webmd.com/content/article/45/1811_50450.htm?, printed Sep. 12, 2003.
Definition of "Chemotherapy," Merriam-Webster Dictionary, electronic edition, http://www.m-w.com/cgi-bin/dictionary, printed Sep. 22, 2003.
Definition of "Chemotherapeutic," Merriam-Webster Dictionary, electronic edition, http://www.m-w.com/cqi-bin/dictionary, printed Sep. 22, 2003.
Simone, J.V. et al, "Part XIV: Oncology," Cecil Textbook of Medicine, Goldman, L. et al, ed., 21$^{st}$ Edition, W.B. Saunders Co., Philadelphia, PA, pp. 1029-1031, (2000).
Bertino, J.R. et al, "Part XIV: Oncology, The Principles of Cancer Therapy" Cecil Textbook of Medicine, Goldman, L. et al, ed., 21$^{st}$ Edition, W.B. Saunders Co., Philadelphia, PA, pp. 1060-1070, (2000).

(Continued)

Primary Examiner—Janet L. Epps-Smith
(74) Attorney, Agent, or Firm—Cook Alex Ltd.

(57) ABSTRACT

New chemotherapeutic medicaments and certain medical uses and methods for use of such chemotherapeutic medicaments for treatment of disease in human or animal tissue are described, wherein a primary active component of such medicaments is a halogenated xanthene or halogenated xanthene derivative. Preferably, the halogenated xanthene is Rose Bengal or a functional derivative of Rose Bengal. The halogenated xanthenes constitute a family of useful chemotherapeutic agents that afford selective, persistent accumulation in certain tissues. In preferred embodiments, such medicaments are used for treatment of a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as connective tissues and various tissue surfaces exposed during surgery, as well as various tissues exhibiting microbial or parasitic infection. In another preferred embodiment, such medicaments are produced in various formulations useful for intracorporeal or topical administration, including in liquid, semisolid, solid or aerosol delivery vehicles.

4 Claims, 4 Drawing Sheets

OTHER PUBLICATIONS

European Search Report dated Apr. 21, 2004 for EP 01 95 4627.
Bottiroli et al. "Enzyme-assisted Cell Photosensitization: A Proposal for an Efficient Approach to Tumor Therapy and Diagnosis," Photochemistry and Photobiology, 1997, 66(3): pp. 374-383.
Floyd J. Green, The Sigma-Aldrich Handbook of Stains. Dyes and Indicators, Aldrich Chemical Company, Inc., Milwaukee, Wisconsin, pp. 304-305; pp. 320-321; pp. 636-637 (1990).
Xanthenes: Fluorone Derivatives, The Journal of Organic Chemistry 57 Jul. 31, 1992, No. 16, Washington, DC pp. 4418-4421.
(Svensk Farmaceutisk Tidskrift (1973) 77 (13): 641-647 (Abstract).
Amendment G of U.S. Appl. No. 09/382,622, filed on Jul. 12, 2007.
Amendment G of U.S. Appl. No. 09/799,785, filed on Jul. 24, 2007.
Preliminary Amendment A of U.S. Appl. No. 11/124,654, filed on May 6, 2005.
Amendment C After Final of U.S. Appl. No. 10/999,313, filed on Jan. 23, 2008.
Amendment J After Final of U.S. Appl. No. 09/635,276, filed on Oct. 15, 2007.
Preliminary Amendment A of U.S. Appl. No. 11/429,742, filed on May 8, 2006.
Claims of U.S. Appl. No. 11/936,963, filed Nov. 8, 2007 and Filing Receipt for this application dated Feb. 15, 2008.
Claims of U.S. Appl. No. 11/715,780, filed Mar. 8, 2008 and Filing Receipt for this application dated May 30, 3007.

* cited by examiner

MEDICAMENTS FOR CHEMOTHERAPEUTIC TREATMENT OF DISEASE

BACKGROUND OF THE INVENTION

This application claims the benefit under 35 USC §119(e) of U.S. application 60/218,464 filed Jul. 14, 2000. This application is also a continuation-in-part of U.S. application Ser. No. 09/130,041, filed on Aug. 6, 1998 now abandoned; U.S. application Ser. No. 09/635,276 filed on Aug. 9, 2000 now abandoned which is a continuation-in-part of U.S. application Ser. No. 09/216,787 filed Dec. 21, 1998 now U.S. Pat. No. 6,331,286; and U.S. application Ser. No. 09/799,785 filed on Mar. 6, 2001, which are herein incorporated by reference in their entirety now U.S. Pat. No. 7,390,668.

The present invention is related to certain chemotherapeutic medicaments and methods for treatment of human or animal tissue using chemotherapy.

Chemotherapy was developed to treat cancer and other disease with the promise of limiting the invasiveness of the therapeutic intervention. Ideally in the practice of chemotherapy, chemical agents that afford selective toxicity to diseased or otherwise undesirable tissue are administered to a patient. Frequently, these agents are administered systemically, with the expectation that the viability of certain tissues, such as the rapidly proliferating tissues of a cancerous tumor, will be selectively inhibited or destroyed. Unfortunately, most chemotherapeutic agents presently available offer limited specificity for such tissue, resulting in a high incidence of disagreeable side-effects, such as immune system suppression, nausea, and hair loss. While tremendous strides have been made in an effort to reduce or mitigate such side-effects, there still continues to be great difficulty in enhancement of specificity of the drug for tissues to be treated.

Therefore, it is an object of the present invention to provide new chemotherapeutic medicaments, new medical uses for such medicaments based on improved specificity of such medicaments for the desired target tissue to be treated, and methods for treatment using such medicaments, thereby resulting in improved treatment outcomes, increased efficacy and safety and reduced cost of treatment.

SUMMARY OF THE PRESENT INVENTION

The present invention is directed to new chemotherapeutic medicaments and certain medical uses of such medicaments, and methods for treatment using such medicaments, for treatment of human or animal tissue, wherein a primary active component of such medicaments is a halogenated xanthene or a halogenated xanthene derivative. In a preferred embodiment, the halogenated xanthene is Rose Bengal or a functional derivative of Rose Bengal. The halogenated xanthenes constitute a family of extremely useful agents that can be selectively delivered at high concentrations to certain tissues. Selective retention of such agents at high concentrations in the desired tissues results in decreased viability or death of such tissues (and hence provides a chemotherapeutic use of medicaments containing agents). Such medicaments are suitable for intracorporeal administration, and are thus intracorporeal chemotherapeutic medicaments. Such medicaments are also suitable for topical administration, and are thus topical chemotherapeutic medicaments. Such medicaments can also be called pharmaceutical compositions or agents.

Such chemotherapeutic medicaments are useful for the treatment of a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as connective tissues and various tissue surfaces exposed during surgery, as well as various tissues exhibiting microbial, viral, fungal or parasitic infection. These medicaments are available in various formulations that may include liquid, semisolid, solid or aerosol delivery vehicles, and are suitable for intracorporeal administration via various conventional modes and routes, including intravenous injection (i.v.), intraperitoneal injection (i.p.), intramuscular injection (i.m.), intracranial injection (i.c.), intratumoral injection (i.t.), intraepithelial injection (i.e.), transcutaneous delivery (i.c.), and per oesophageal (p.o.) administration. Additionally, such medicaments are suitable for topical administration via various conventional modes and routes, including topical application directly to or proximal to certain tissues. The active ingredients in such chemotherapeutic medicaments produce a desirable therapeutic response, such as destruction of microbial infection, reduction or elimination of tissue irritation, reduction or elimination of hyperproliferative tissue, reduction or elimination of cancerous or precancerous tissue, reduction or elimination of surface or subsurface lipocytes or lipid deposits, and many other similar indications.

In a preferred embodiment, such chemotherapeutic medicaments are used for treatment of a variety of conditions affecting the skin and related organs.

In another preferred embodiment, such chemotherapeutic medicaments are used for treatment of a variety of conditions affecting the mouth and digestive tract and related organs.

In another preferred embodiment, such chemotherapeutic medicaments are used for treatment of a variety of conditions affecting the urinary and reproductive tracts and related organs.

In another preferred embodiment, such chemotherapeutic medicaments are used for treatment of a variety of conditions affecting the respiratory system and related organs.

In another preferred embodiment, such chemotherapeutic medicaments are used for treatment of a variety of conditions affecting the circulatory system and related organs.

In another preferred embodiment, such chemotherapeutic medicaments are used for treatment of a variety of conditions affecting the head and neck.

In another preferred embodiment, such chemotherapeutic medicaments are used for treatment of a variety of conditions affecting the endocrine and lymphoreticular systems and related organs.

In another preferred embodiment, such chemotherapeutic medicaments are used for treatment of a variety of conditions affecting various other tissues, such as connective tissues and various tissue surfaces exposed during surgery.

In another preferred embodiment, such chemotherapeutic medicaments are used for treatment of a variety of conditions related to microbial or parasitic infection.

In another preferred embodiment, such chemotherapeutic medicaments are produced in various formulations including liquid, semisolid, solid or aerosol delivery vehicles, as well as in tablet, capsule, suppository, and other similar forms.

BRIEF DESCRIPTION OF THE DRAWINGS

In describing the preferred embodiments, reference is made to the accompanying drawings wherein.

DETAILED DESCRIPTION OF THE PRESENTLY PREFERRED EMBODIMENTS

Figure 1A:
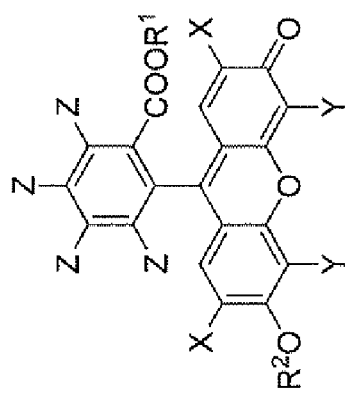
FIG. 1(a) shows the generalized chemical structure of the halogenated xanthenes.

The present invention is directed to new chemotherapeutic medicaments and certain medical uses of such chemotherapeutic medicaments, and methods for chemotherapeutic treatment using such medicaments, for treatment of human or animal tissue, wherein a primary active component of such medicaments is a halogenated xanthene or halogenated xanthene derivative The inventors of the present invention have discovered that such halogenated xanthenes, as discussed in more detail infra, exhibit desirable chemotherapeutic effects when applied to or otherwise delivered to certain human or animal tissues. The desirable effects include reduction or elimination of disease or diseased tissue or other undesirable conditions, including eradication of cancerous or pre-cancerous tumors and infectious agents. The treatment is applicable to a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as tissues exposed during surgery, as well as various tissues exhibiting microbial, viral, fungal or parasitic infection.

In a preferred embodiment, such medicaments are produced in various formulations suitable for intracorporeal or topical administration, including in various liquid, semisolid, solid or aerosol delivery vehicles, as well as in tablet, capsule, suppository, and other similar forms. Such medicament formulations are suitable for delivery via various conventional modes and routes (hereafter defined as administration), including intravenous injection (i.v.), intraperitoneal injection (i.p.), intramuscular injection (i.m.), intracranial injection (i.c.), intratumoral injection (i.t.), intraepithelial injection (i.e.), transcutaneous delivery (t.c.), per oesophageal (p.o.) administration, and topical application; additional administrative modes and routes include intraabdominal, intraapendicular, intraarterial, intraarticular, intrabronchial, intrabuccal, intracapsular (such as for example capsule in knee, elbow and eye), intracardial, intracartilaginous, intracavitary, intracephalic, intracolic, intracutaneous, intracystic, intradermal, intraductal, intraduodenal, intrafascicular, intrafat, intrafilar, intrafissural, intragastric, intraglandular, intrahepatic, intraintestinal, intralamellar, intralesional, intraligamentous, intralingual, intramammary, intramedullary, intrameningeal, intramyocardial, intranasal, intraocular, intraoperative, intraoral, intraosseous, intraovarian, intrapancreatic, intraparietal, intrapelvic, intrapericardial, intraperineal, intraperitoneal, intraplacental, intrapleural, intrapontine, intraprostatic, intrapulmonary, intrarachidian, intrarectal, intrarenal, intrascleral, intrascrotal, intrasegmental, intrasellar, intraspinal, intrasplenic, intrastemal, intrastromal, intrasynovial, intratarsal, intratesticular, intrathoracic, intratonsillar, intratracheal, intratubal, intratympanic, intraureteral, intraurethral, intrauterine, intravaginal, intravascular, intraventricular, intravertebral, intravesical, or intravitreous administration.

1. Properties of the Preferred Active Components and Medicament Formulations.

The inventors of the present invention have discovered a class of agents that are broadly applicable for producing chemotherapeutic medicaments for treatment of disease in certain human and animal tissues. These agents are referred to as halogenated xanthenes and are illustrated in FIG. 1a, where the symbols X, Y, and Z represent various elements present at the designated positions, and the symbols $R^1$ and $R^2$ represent various functionalities present at the designated positions.

Selected properties (such as chemical constituents at positions X, Y, and Z and functionalities $R^1$ and $R^2$) of representative halogenated xanthenes are summarized in attached Table 1. Certain general properties of this class of agent are discussed in further detail in U.S. Ser. No. 09/130,041 filed on Aug. 6, 1998, U.S. Ser. No. 09/184,388 filed on Nov. 2, 1998, U.S. Ser. No. 09/216,787 filed on Dec. 21, 1998, U.S. Ser. No. 09/635,276 filed on Aug. 9, 2000, U.S. Ser. No. 09/799,785 filed Mar. 6, 2001, and U.S. Ser. No. 09/817,448 filed Mar. 26, 2001, which are herein incorporated by reference in their entirety. In general, the halogenated xanthenes are characterized by a low cytotoxicity (toxicity to cells) at low concentration, a propensity for selective concentration or retention in certain tissues and cells, a high cytotoxicity upon such concentration or retention, and by chemical and physical properties that are substantially unaffected by the local chemical environment or by the attachment of functional derivatives at positions $R^1$ and $R^2$. Such factors make these chemical agents, and in particular chemotherapeutic medicaments formulated from such agents, excellent for the treatment of disease in human and animal tissues.

It is thus one preferred embodiment of the present invention that a chemotherapeutic medicament be produced that contains, as an active ingredient at a concentration of from greater than approximately 0.001% to less than approximately 20%, at least one halogenated xanthene.

Figure 1B:
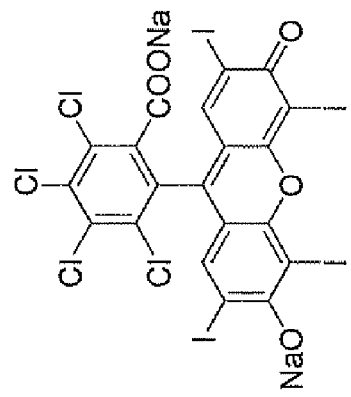
FIG. 1(b) shows the chemical structure of Rose Bengal.

It is preferred that this medicament include the halogenated xanthene Rose Bengal (4,5,6,7-Tetrachloro-2',4',5',7'-tetraiodofluorescein, illustrated in FIG. 1b).

Examples of other halogenated xanthenes which can be used in the medicaments of the present invention include one or more of the following Fluorescein derivatives: 4',5'-Dichlorofluorescein; 2',7'-Dichlorofluorescein; 4,5,6,7-Tetrachlorofluorescein; 2',4',5',7'-Tetrachlorofluorescein; Dibromofluorescein; Solvent Red 72; Diiodofluorescein; Eosin B; Eosin Y; Ethyl Eosin; Erythrosin B; Phloxine B; Rose Bengal; 4,5,6,7-Tetrabromoerythrosin; Mono-, Di-, or Tribromoerythrosin; Mono-, Di-, or Trichloroerythrosin; Mono-, Di-, or Trifluoroerythrosin; 2',7'-Dichloro-4,5,6,7-Tetrafluorofluorescein; 2',4,5,6,7,7'-Hexafluorofluorescein, 4,5,6,7-Tetrafluorofluorescein, 2',4',5,5',6,7'-Hexaiodofluorescein; 2',4',5,5',7,7'-Hexaiodofluorescein; 2',4',5',6,7,7'-Hexaiodofluorescein; 2',4,5,5',6,7,7'-Heptaiodofluorescein; 4-Chloro-2',4',5,5',6,7'-hexaiodofluorescein; 4-Chloro-2',4',5,5',7,7'-hexaiodofluorescein; 4-Chloro-2',4',5',6,7,7'-hexaiodofluorescein; 4-Chloro-2',4',5,5',6,7,7'-heptaiodofluorescein; 4,5-Dichloro-2',4',5',6,7,7'-hexaiodofluorescein; 4,6-Dichloro-2',4',5,5',7,7'-hexaiodofluorescein; and 4,7-Dichloro-2',4',5,5',6,7'-hexaiodofluorescein.

As an example of these desirable chemical, biochemical, and physical properties, the inventors have found that the prototypical halogenated xanthene, Rose Bengal, will accumulate preferentially in (e.g., target) some tumors and other tissues and pathogenic entities and exhibit high cytotoxicity within such tumors, tissues and pathogenic entities, while exhibiting negligible systemic cytotoxicity or local cytotoxicity in surrounding healthy tissues. Such agents also possess the ability to clear rapidly from healthy tissue in the body. Furthermore, such agents have a relatively low cost.

For example, to a first approximation, an agent's potential for tissue accumulation can be estimated based on the partition coefficient, $K_p$. This in vitro parameter is purported to have predictive value relating to in vivo agent delivery at the cellular level. In particular, a value greater than unity is considered to indicate agents capable of localizing in tumor or other diseased tissue, and thereby being capable of exhibiting enhanced chemotherapeutic efficacy in such tissue. $K_p$ is determined by measuring the ratio of equilibrium concentrations of an agent in a lipophilic phase (n-octanol) contacted with an aqueous phase (phosphate buffered saline, PBS, pH=7.4). Comparative values of $K_p$ are shown in Table 2. The large $K_p$ values for the halogenated xanthenes suggest that the halogenated xanthenes will exhibit a preference for concentration or accumulation in tumor or other diseased tissue, and should thereby be capable of exhibiting superior chemotherapeutic efficacy in such tissue. However, as explained below, the inventors have discovered that halogenated xanthenes exhibit a much greater chemotherapeutic efficacy in such tissue than could be predicted solely from the $K_p$ values shown in Table 2.

Figure 2:
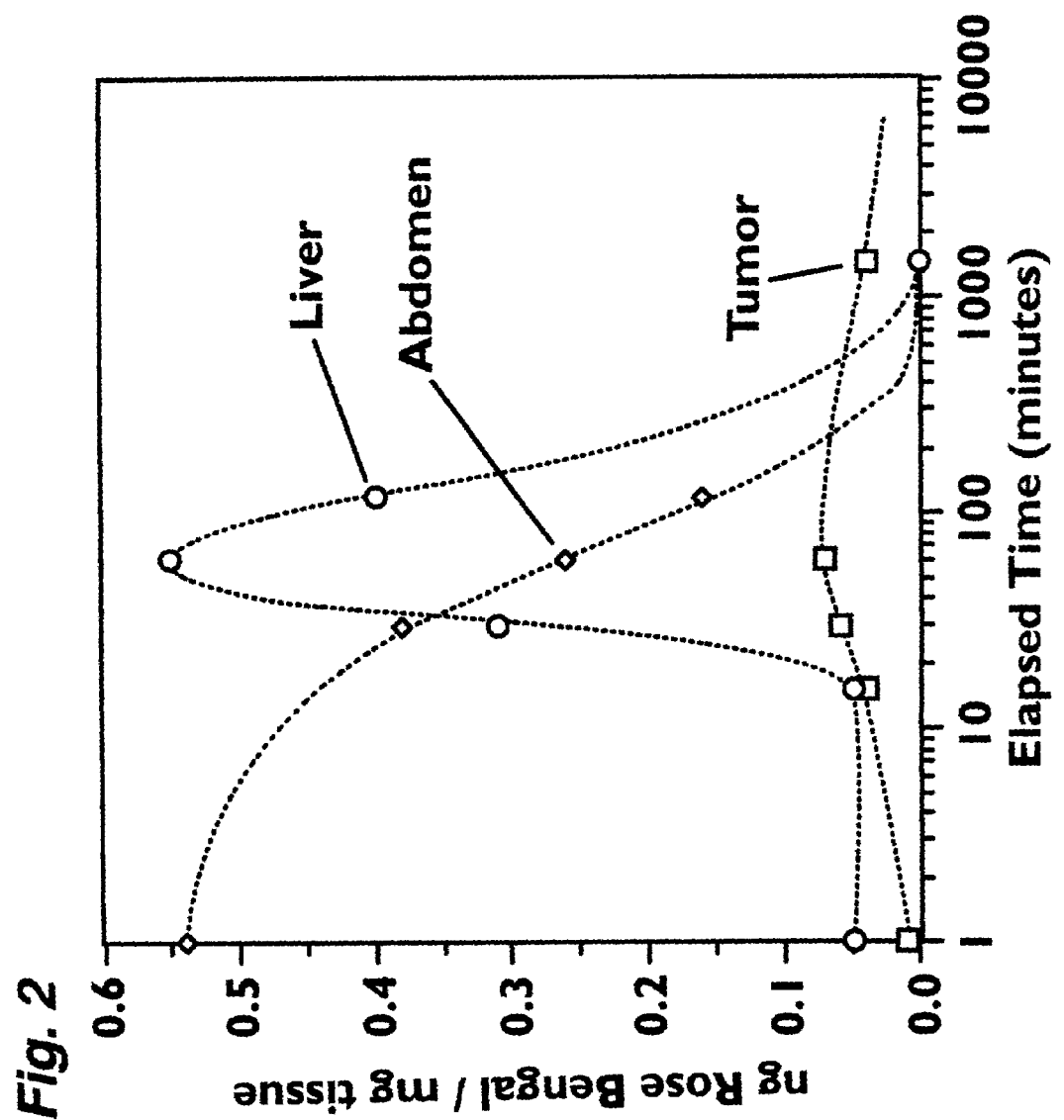
FIG. 2 shows example pharmacokinetic behavior of Rose Bengal upon intraperitoneal injection into nude mice with an implanted MCF-7 human breast cancer tumor.

The following examples illustrate this preference for accumulation in tumor tissue by the halogenated xanthenes:

Tumor cell suspensions (e.g., melanoma, breast tumor, liver tumor, renal carcinoma, gall bladder tumor or prostate tumor) were injected subcutaneously into the flanks of nude mice and resulted in the formation of primary tumors, within a few weeks, at the injection site having a volume of approximately 0.25 cm$^3$. A solution of Rose Bengal (50-100 µL of 0.5% Rose Bengal in saline) was then administered by intraperitoneal injection (i.p.) to the tumor-bearing mice, and the injected mice sacrificed at timed intervals following injection. Tissue samples (liver, abdominal wall, and tumor) were immediately obtained from the sacrificed mice, homogenized, centrifuged for 10 minutes at 1520×g, and the resulting supernatant collected and analyzed fluorimetrically. This allowed the pharmacokinetics of the administered Rose Bengal to be easily observed, as illustrated in FIG. 2. The data in FIG. 2 show that Rose Bengal rapidly diffuses from normal tissue (e.g, abdominal wall) and is efficiently entrapped and excreted through the liver, with concentrations in these tissues diminishing to unmeasurable levels within 24 hours. At the same time, persistent accumulation occurs in tumor tissue, with greater than 50% of maximum measured agent concentration maintained in such tissues for periods in excess of 24 hours.

If such implanted tumors are directly injected with Rose Bengal, similar selective, persistent accumulation occurs.

For example, BNL/SV40 liver cell tumor cells injected into the flanks of nude mice, as described supra, resulted in the formation of primary tumors, within a few weeks, at the injection site and have a volume of approximately 0.25 cm$^3$. Intratumoral (i.t.) and peritumoral (p.t.) injection of a 10% solution of Rose Bengal (50 µL of 10% Rose Bengal in saline) resulted in marked red staining of the tumor and the surrounding flank. Within 7 days this Rose Bengal cleared from normal tissue, but the tumor tissue remained stained. Over a period of several weeks the previously rapidly growing tumor exhibited stasis, with no significant change in tumor volume and a marked absence of mitotic figures (e.g., exhibiting only non-hyperproliferative cells).

Further, peritumoral injection alone (e.g., injection into normal tissue around the outside margins of the tumor) of the above Rose Bengal exhibited no detectable retention in normal tissue after 24 hours. Notably, no significant effect on normal tissue, nor on the adjacent tumor tissue, was noted upon peritumoral injection alone.

Hence, the administered Rose Bengal in these examples not only exhibited selective, persistent accumulation in tumor tissue, but this accumulated agent also exhibits chemotherapeutic efficacy with minimal or no measurable side effects in healthy tissue.

This chemotherapeutic effect for Rose Bengal is further illustrated by the following example. An adult, female dog with a naturally-occurring, recurrent aggressive sarcoma tumor (approximately 20 cc in volume) was treated by injection of approximately 5 cc of a 10% solution of Rose Bengal at several locations throughout the tumor volume. After a period of five days, a follow-up examination of the animal indicated a measurable decrease in tumor density along with significant edema and apparent necrosis of large sections of the tumor. Another follow-up examination after 19 days indicated a further measurable decrease in tumor size. Such a response is indicative of chemotherapeutic activity of the injected Rose Bengal within the tumor mass. It is also notable that no significant side-effects were noted in the healthy tissue surrounding the tumor.

In contrast, i.t. administration of a different class of agent, indocyanine green ($K_p$=99), into various murine tumors showed that within 24 hours this agent substantively migrates out of tumors, with residual agent tending to accumulate in peritumoral tissues. Moreover, no chemotherapeutic effect was evidenced upon such administration of such agent. Hence, while the $K_p$ value for indocyanine green is nearly ten-fold larger than that of Rose Bengal (and as such, indocyanine green is, by the conventional model based solely on $K_p$, expected to accumulate strongly in tumor tissue), the tissue localization properties of the two agents are clearly completely different. Furthermore, even at the relatively high concentrations in the immediate vicinity of the injection site, indocyanine green was found to exhibit no chemotherapeutic activity.

Thus, the halogenated xanthenes, and in particular Rose Bengal, exhibit an unexpectedly marked preference for selective accumulation and retention in tumor and other diseased tissue upon administration, and that once present in such tissue, said halogenated xanthenes can be utilized as potent, highly tissue- or disease-specific chemotherapeutic agents.

The toxicology data shown in Table 2 indicate that the halogenated xanthenes are relatively non-toxic, and yet, in contrast to agents such as indocyanine green, they exhibit unanticipated chemotherapeutic properties. One possible explanation for this may be that such chemotherapeutic properties of the halogenated xanthenes, and in particular of Rose Bengal, are the result of their special combination of modest intrinsic cytotoxicity and marked propensity for persistent, selective accumulation in certain cells, such as cancerous cells: based, for example, on simple first-order kinetics, such modestly cytotoxic agents, upon becoming present in cells at high local concentrations for extended periods of time, should exhibit chemotherapeutic properties.

Figure 3:
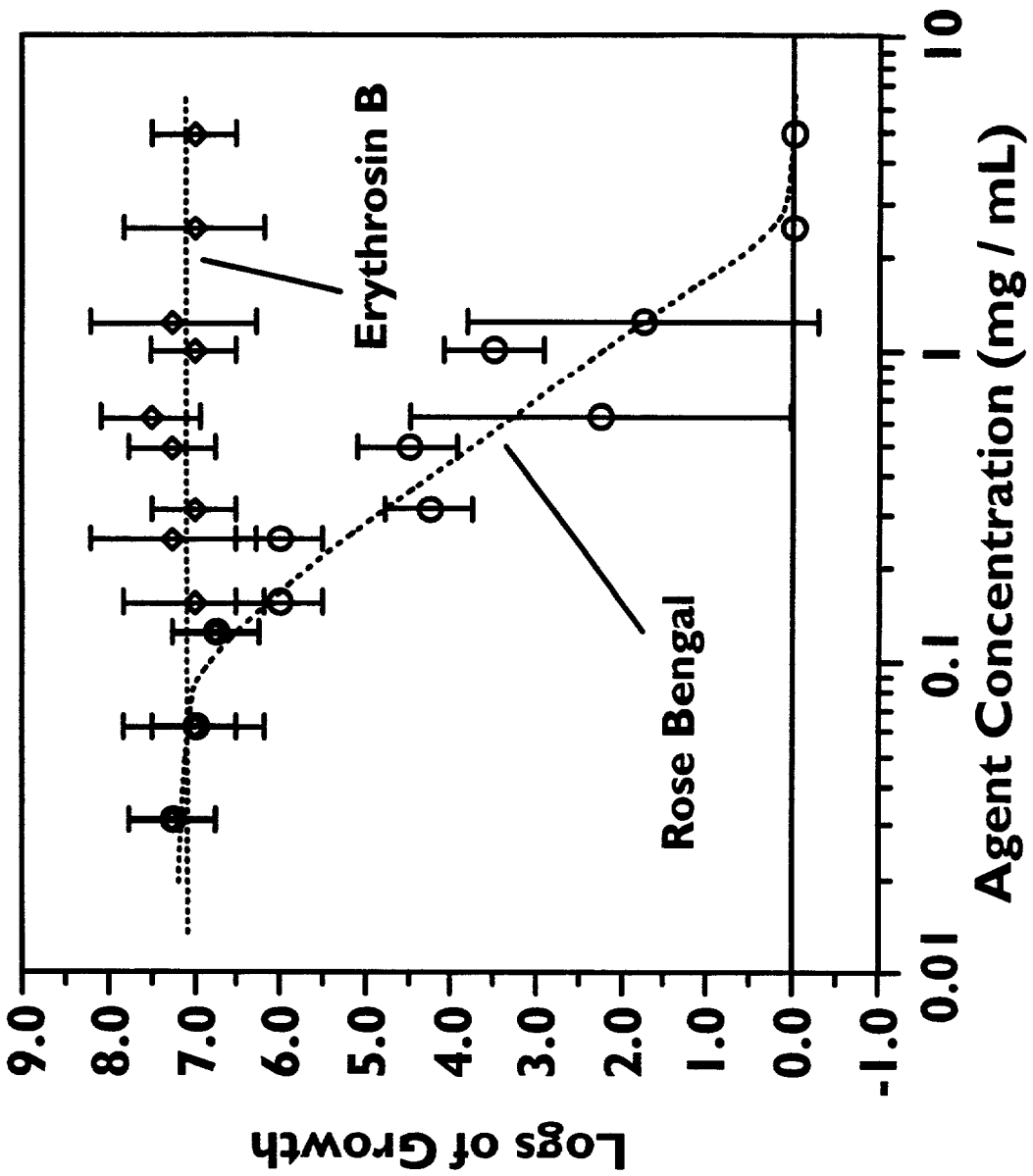
FIG. 3 illustrates cytotoxic effects in bacteria upon exposure to either Rose Bengal or Erythrosin B as a function of agent concentration.
Figure 4:
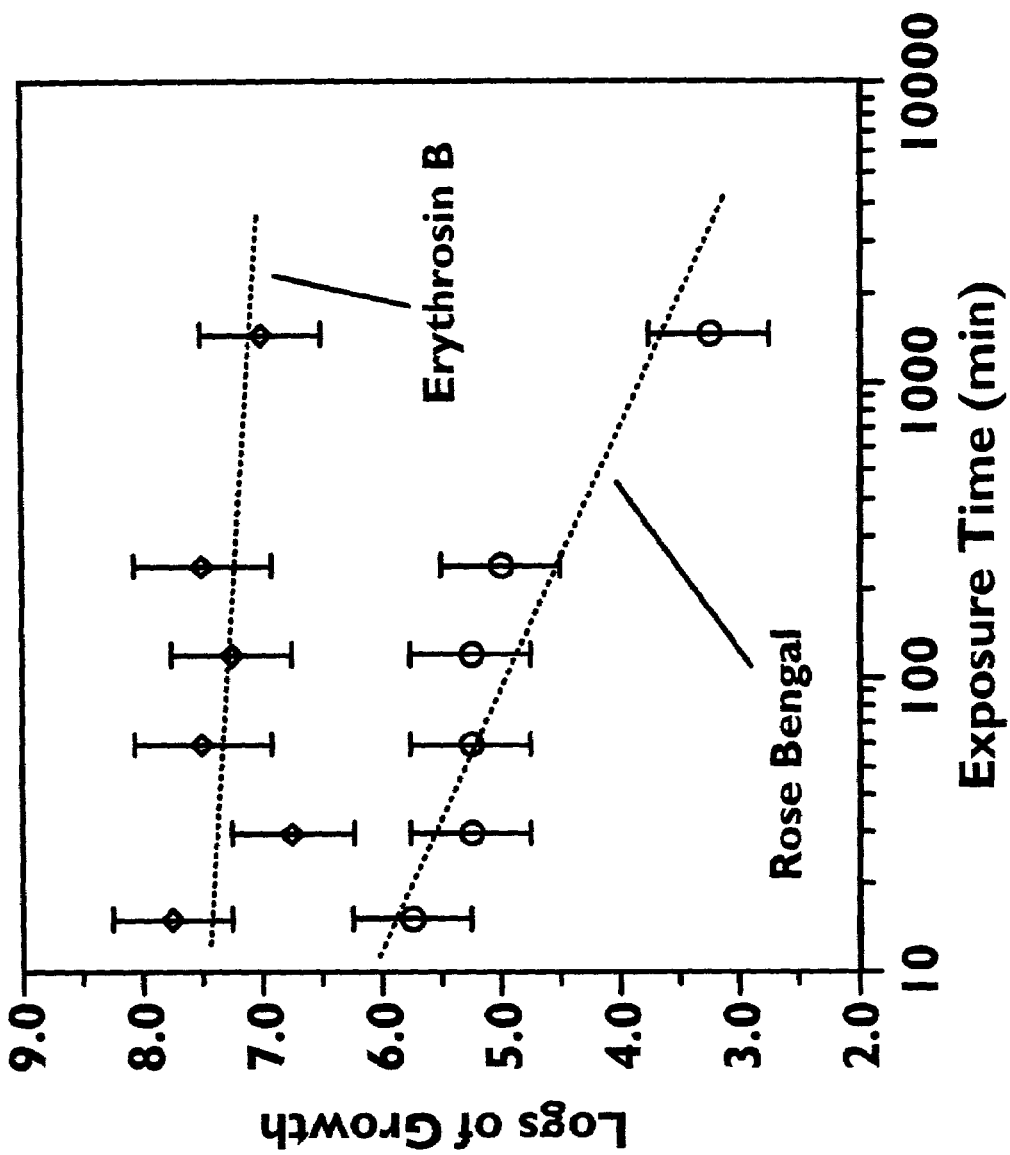
FIG. 4 illustrates the cytotoxic effects of exposure to either Rose Bengal or Erythrosin B as a function of exposure duration.

The inventors tested this hypothesis by evaluating the chemotherapeutic properties of Rose Bengal and Erythrosin B on cultures of the bacterium *Staphylococcus aureus*. These data are illustrated in FIGS. 3 and 4. In both illustrations, test cultures were exposed to the indicated agents at the indicated concentrations for the indicated times; cytotoxicity was subsequently estimated by serial dilution (10× dilution per step)

of the treated cell cultures into 96-well plates containing fresh culture media; these samples were then incubated under standard conditions. Viability (e.g., Logs of Growth) for each test culture was then estimated by counting the number of dilution steps resulting in positive cell growth. Cytotoxicity upon exposure to a particular agent is thereby estimated by the reduction in viability relative to unexposed (e.g., control) cultures. FIG. 3 illustrates the cytotoxic effects of a 90 minute exposure of S. aureus to either Rose Bengal or Erythrosin B. In this figure, Rose Bengal exhibits a marked chemotherapeutic response that is concentration dependent, while Erythrosin B exhibits no significant chemotherapeutic response for this brief exposure duration over the range of concentrations tested. FIG. 4 illustrates the cytotoxic effects on S. aureus for various durations of exposure to Rose Bengal or Erythrosin B (each administered at a concentration of 0.5 mg/mL). These data show that the chemotherapeutic properties of the halogenated xanthenes are dependent on exposure time. Notably, the negative slopes for the trend lines of both agents are indicative of cumulative cytotoxicity that is time dependent. The shallower slope for Erythrosin B indicates lower cytotoxicity in this model (e.g. S. aureus), consistent with the results illustrated in FIG. 3. Hence, certain agents that exhibit a modest, but nonetheless finite, cytotoxicity (such as for example, but not limited to, the halogenated xanthenes) should afford chemotherapeutic modality when administered to certain tissues, wherein such administration results in sufficient local concentration of such agents for a sufficient period so as to cause local cytotoxic effects (e.g., chemotherapy) in such tissues.

In addition to superior suitability for direct administration into desired targeted tissue to be treated, such as a focal tumor, the preference of the halogenated xanthenes for accumulation in certain types of tissues provides a basis for highly-selective, systemic delivery of the halogenated xanthenes to such tissues. For example, Rose Bengal's relatively large partition coefficient is indicative of a preference for accumulation in lipophilic tissue, such as cutaneous lipocytes. Systemic administration of Rose Bengal, for example as an aqueous solution administered via intraperitoneal injection (i.p.) or per oesophagus (p.o.) administration, resulted in highly selective accumulation of said agent in certain tissues, such as in the cutaneous fat deposits of obese laboratory mice. Histologic examination of skin samples from such animals showed that the accumulated agent was substantively limited to cutaneous lipocytes.

Moreover, the facility with which the halogenated xanthenes target specific tissues or other sites can be further optimized by attachment of specific functional derivatives at positions $R^1$ and $R^2$, so as to change the chemical partitioning and/ or biological activity of the agent. For example, attachment of one targeting moiety or more at positions $R^1$ or $R^2$ can be used to improve targeting to specific tissues, such as cancerous tumor tissues or sites of localized infection. An example of this is esterification at position $R^1$ with a short aliphatic alcohol, such as n-hexanol, to produce a derivatized agent exhibiting enhanced partitioning into lipid-rich tumor tissues.

It is thus a further preferred embodiment that at least one of the at least one halogenated xanthene active ingredients includes at least one targeting moiety selected from a group that includes deoxyribonucleic acid (DNA), ribonucleic acid (RNA), amino acids, proteins, antibodies, ligands, haptens, carbohydrate receptors or complexing agents, lipid receptors or complexing agents, protein receptors or complexing agents, chelators, encapsulating vehicles, short- or long-chain aliphatic or aromatic hydrocarbons, including those containing aldehydes, ketones, alcohols, esters, amides, amines, nitriles, azides, or other hydrophilic or hydrophobic moieties. A further example of this embodiment is derivatization of Rose Bengal with a lipid (at position $R^1$, via esterification), so as to increase the lipophilicity of Rose Bengal, and thereby modify its targeting properties in a patient. An additional further example of this embodiment is derivatization of Rose Bengal with folate (at position $R^1$, via esterification or other modes of attachment), so as to increase selective targeting of cancer and other cells exhibiting enhanced folate receptor activity or folate metabolism.

As a further example of the desirable chemical, biochemical, and physical properties of the halogenated xanthenes and halogenated xanthene derivatives, the inventors of the present invention have shown that these agents are readily cleared from healthy tissues in a matter of several hours, and are rapidly excreted in bile, urine and feces, without doing damage to healthy tissue while in the body. Further examples of the desirable properties of the halogenated xanthenes and halogenated xanthene derivatives are that the halogenated xanthenes and halogenated xanthene derivatives are easily synthesized using simple, low-cost synthetic methods, can be readily purified, and exhibit excellent stability (such as a long shelf life without need for refrigeration or storage under an inert atmosphere).

Because the halogenated xanthenes and their derivatives are, in general, fine solid powders in their pure form, it is preferred that, for proper delivery to desired tissues, such agents be formulated in appropriate delivery vehicles. Specifically, such formulations are preferred so as to facilitate agent delivery into the body and subsequent contact with, and delivery to, desired tissues to be treated. Approaches to such formulation will be generally known to those of ordinary skill in the art.

It is thus a further preferred embodiment of the present invention that at least one halogenated xanthene or halogenated xanthene derivative be formulated as a medicament in a form suitable for intracorporeal or topical administration via various conventional modes and routes. Such suitable forms include, for example, medicaments formulated in a liquid, semisolid, solid or aerosol delivery vehicle, including in vehicles of the following natures: aqueous, non-aqueous or particulate suspensions, solutions, creams, ointments, gels, syrups, micro-droplet sprays, suppositories, tablets and capsules. The at least one halogenated xanthene or halogenated xanthene derivative may be dissolved or suspended in such delivery vehicle, wherein this vehicle may, in addition to the at least one halogenated xanthene or halogenated xanthene derivative, include various builders, stabilizers, emulsifiers or dispersants, preservatives, buffers, electrolytes, and tissue penetrating or softening agents. Such components of the delivery vehicle may be present as the primary component (by weight or volume) of the medicament, or as a minor component that serves in an adjuvant role in agent delivery with no adverse affect on tissue or treatment outcome.

Examples of appropriate builders include cellulose and cellulose derivatives, such as starch, and alginates.

Examples of appropriate stabilizers, emulsifiers or dispersants include liposomes, nanoparticulates and nanodispersions, microparticulates and microdispersions, as well as various lipids, detergents and other surfactants.

Examples of appropriate preservatives include benzalkonium chloride, thimerosal, quaternary amines and urea.

Examples of appropriate buffers include monobasic or dibasic phosphate salts, citrate salts, bicarbonate salts, and ethanolamine.

Examples of appropriate electrolytes include sodium, potassium, calcium and magnesium chlorides, phosphates, and nitrates.

Examples of appropriate tissue penetrating, softening or solvating agents and adjuvants include:

- various sulfoxides, such as DMSO and decylmethylsulfoxide;
- various aliphatic and fatty alcohols, such as ethanol, propanol, hexanol, octanol, benzyl alcohol, decyl alcohol, lauryl alcohol, and stearyl alcohol;
- various linear and branched, saturated and unsaturated fatty acids, such as lauric acid, caproic acid, capric acid, myristic acid, stearic acid, oleic acid, isovaleric acid, neopentanoic acid, trimethyl hexanoic acid, neodecanoic acid and isostearic acid;
- various aliphatic and alkyl fatty acid esters, such as isopropyl n-butyrate, isopropyl n-hexanoate, isopropyl n-decanoate, isopropyl myristate, isopropyl palmitate, octyldodecyl myristate, ethyl acetate, butyl acetate, methyl acetate, methylvalerate, methylpropionate, diethyl sebacate and ethyl oleate;
- various polyols, such as propylene glycol, polyethylene glycol, ethylene glycol, diethylene glycol, triethylene glycol, diproplyene glycol, glycerol, propanediol, butanediol, pentanediol and hexanetriol;
- various amides, such as urea, dimethylacetamide, diethyltoluamide, dimethylformamide, dimethyloctamide, dimethyldecamide; biodegradable cyclic urea, such as 1-alkyl-4-imidazolin-2-one; pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methyoxycarbonyl-2-pyrrolidone, 1-methyl-4-methyoxycarbonyl-2-pyrrolidone, 1-lauryl-4-methyoxycarbonyl-2-pyrrolidone, N-cyclohexylpyrrolidone, N-dimethylaminopropylpyrrolidone, N-cocoalkypyrrolidone, N-tallowalkylpyrrolidone; biodegradable pyrrolidone derivatives, such as fatty acid esters of N-(2-hyroxyethyl)-2-pyrrolidone; cyclic amides, such as 1-dodecylazacycloheptane-2-one (Azone®), 1-geranylazacycloheptan-2-one, 1-farnesylazacycloheptan-2-one, 1-geranylgeranylazacycloheptan-2-one, 1-(3,7-dimethyloctyl) azacycloheptan-2-one, 1-(3,7,11-trimethydodecyl)azacycloheptan-2-one, 1-geranylazacyclohexane-2-one, 1-geranylazacyclopentan-2,5-dione, 1-farnesylazacyclopentan-2-one; hexamethylenelauramide and its derivatives; and diethanolamine and triethanolamine;
- various surfactants, such as anionic surfactants, including sodium laurate and sodium lauryl sulfate; cationic surfactants, including cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride; nonionic surfactants, such as Polaxamer (231, 182, 184), Brij (30, 93, 96, 99), Span (20, 40, 60, 80, 85), Tween (20, 40, 60, 80), Myrj (45, 51, 52), Miglyol 840; various bile salts, such as sodium cholate, sodium salts of taurocholic, glycholic, desoxycholic acids; lecithin;
- various terpenes, including hydrocarbons, such as D-limonene, α-pinene, β-carene; various terpene alcohols, including α-Terpineol, terpinen-4-ol, carvol; various terpene ketones, including carvone, pulegone, piperitone, menthone; various terpene oxides, including cyclohexane oxide, limonene oxide, o-pinene oxide, cyclopentene oxide, 1,8-cineole; various terpene oils, including ylang ylang, anise, chenopodium, eucalyptus;
- various alkanones, such as N-heptane, N-octane, N-nonane, N-decane, N-undecane, N-dodecane, N-tridecane, N-tetradecane, N-hexadecane;
- various organic acids, such as salicylic acid and salicylites (including their methyl, ethyl, and propyl glycol derivatives), citric and succinic acid.

The present invention is not limited to the above recited examples, as other formulations familiar to those of ordinary skill in the art, including various simple or complex combinations of vehicles and adjuvants, are also useful for improving delivery of the photoactive component of the medicament to target tissues.

2. Methods and Medical Use of the Subject Medicament for Chemotherapeutic Treatment of Conditions Affecting the Skin and Related Organs.

The medicaments disclosed herein are broadly applicable to improved chemotherapeutic treatment of various conditions affecting the skin and related organs of humans and animals. The medicament can be applied, using conventional intracorporeal or topical administration modes, directly or indirectly to, or substantially proximal to, tissues to be treated, including those of the skin, nails and scalp. Such administration modes provide direct delivery of medicament to, into or substantially proximal to, tissues to be treated, or systemic delivery of medicament to, into or substantially proximal to, tissues to be treated.

Example indications include treatment for: Psoriasis and Pustular Psoriasis; Reiter's Syndrome; Skin Ulcers, including Stasis Dermatitis, Stasis Ulcers, Ischemic Ulcers, Sickle Cell Leg Ulcers, Diabetic Ulcers, Inflammatory Ulcers; Eczematous Disease and Eczematous Reaction; various Ichthyoses; Atopic Dermatitis; Superficial Wrinkles; Near Surface Fat Reduction; Benign and Malignant Proliferative Disorders, such as Benign Epithelial Tumors and Hamartomas; Premalignant and Malignant Epithelial Tumors, including Actinic Keratoses, Basal Cell Carcinoma, Squamous Cell Carcinoma, and Keratoacanthoma; Benign and Malignant Adnexal Tumors; Tumors of Pigment-Producing Cells, including Malignant Melanoma, Solar Lentigines, Nevi, and Café-au-lait; Sarcomas; Lymphomas; Vascular Disorders, such as Hemangiomas and Port Wine Stain; Microbial Infection, such as Bacterial, Fungal, Yeast, Parasitic or Other Infections; Warts; and Acne. These examples are provided for illustrative purposes, as the present invention is not limited to the recited examples and includes other indications known to those skilled in the art.

3. Methods and Medical Use of the Subject Medicament for Chemotherapeutic Treatment of Conditions Affecting the Mouth and Digestive Tract and Related Organs.

The medicaments disclosed herein are broadly applicable to improved chemotherapeutic treatment of various conditions affecting the mouth and digestive tract and related organs of humans and animals. The medicament can be applied, using conventional intracorporeal or topical administration modes, directly or indirectly to, or substantially proximal to, tissues to be treated, including those of the mouth, gums, tongue, larynx, pharynx, esophagus, stomach, intestines and colon. Such administration modes provide direct delivery of medicament to, into or substantially proximal to, tissues to be treated, or systemic delivery of medicament to, into or substantially proximal to, tissues to be treated.

Example indications include treatment for: Benign Esophageal Lesions, Barretts Esophagus and other Esophageal Hyperplasia and Dysplasia, and Esophageal Cancer, including Squamous Cell Carcinoma, Adenocarcinoma, Carsinosarcoma, Pseudosarcoma, and Sarcoma; Gastric Ulcers, Leiomyomas, Polyps, Neoplasms, Lymphoma and Pseudolymphoma, Adenocarcinoma, Primary Lymphoma, Leiomyosarcoma; Oral and Oropharynx Cancer and Premalignancies, Ulcers and Inflammatory Lesions, including Squamous Cell Carcinoma, Lymphoma, Actinic Cheilitis, Nicotine Stomatitis, Leukoplakia, Erythroplakia; Gum and Other Peridontal Disease, including Gingivitis; Laryngeal Hyperplasia, Dysplasia and Neoplasms; Colorectal Cancer and Polyps. These examples are provided for illustrative purposes, as the present invention is not limited to the recited examples and includes other indications known to those skilled in the art.

4. Methods and Medical Use of the Subject Medicament for Chemotherapeutic Treatment of Conditions Affecting the Urinary and Reproductive Tracts and Related Organs.

The medicaments disclosed herein are broadly applicable to improved chemotherapeutic treatment of various conditions affecting the urinary and reproductive tract and related organs of humans and animals. The medicament can be applied, using conventional intracorporeal or topical administration modes, directly or indirectly to, or substantially proximal to, tissues to be treated, including those of the urethra, bladder, ureter, kidneys, vulva, vagina, cervix, uterus, fallopian tubes, ovaries, penis, testes, vas deferens, prostate, and epididymis. Such administration modes provide direct delivery of medicament to, into or substantially proximal to, tissues to be treated, or systemic delivery of medicament to, into or substantially proximal to, tissues to be treated.

Example indications include treatment for: Urinary Tract Disease, including Cancerous and Pre-Cancerous Hyperplasia, Dysplasia and Neoplasms, Tumors and other Growths, Inflammation, and Infection of the Bladder, Ureter, Urethra, and Kidney; Cancerous and Pre-Cancerous Hyperlasia, Dysplasia and Neoplasms, Tumors and other Growths, Inflammation, and Infection of the Cervix, Endometrium, Myometrium, Ovaries, Fallopian Tubes, Uterus, Vulva, and Vagina, including Vaginal Warts; Cancerous and Pre-Cancerous Hyperlasia, Dysplasia and Neoplasms, Tumors and other Growths, Inflammation, and Infection of the Prostate and Testes; Cancerous and Pre-Cancerous Hyperlasia, Dysplasia and Neoplasms, Tumors and other Growths, Inflammation, and Infection of the Breast; Reproductive Tract Infections, including *Tinea* Cruris, Candidiasis, Condylomata Acuminata, Molluscum Contagiosum, Genital Herpes Simplex Infection, Lymphogranuloma Venereum, Chancroid, Granuloma Inguinale, Erythrasma; Psoriais; and Lichen Planus and Lichen Sclerosus. These examples are provided for illustrative purposes, as the present invention is not limited to the recited examples and includes other indications known to those skilled in the art.

5. Methods and Medical Use of the Subject Medicament for Chemotherapeutic Treatment of Conditions Affecting the Respiratory Tract and Related Organs.

The medicaments disclosed herein are broadly applicable to improved chemotherapeutic treatment of various conditions affecting the respiratory tract and related organs of humans and animals. The medicament can be applied, using conventional intracorporeal or topical administration modes, directly or indirectly to, or substantially proximal to, tissues to be treated, including those of the lung and alveoli, bronchi, trachea, hypopharynx, larynx, nasopharynx, tear ducts, sinuses and nasal cavities. Such administration modes provide direct delivery of medicament to, into or substantially proximal to, tissues to be treated, or systemic delivery of medicament to, into or substantially proximal to, tissues to be treated.

Example indications include treatment for: Hyperplasia, Dysplasia and Neoplasia, Cancer, Inflammation and Infection of the Nasal Cavity, Paranasal Sinuses, Tear Ducts, Eustachian Tubes, Nasopharynx, Hypopharynx, Larynx, Trachea, Bronchi, Lung and Alveoli. These examples are provided for illustrative purposes, as the present invention is not limited to the recited examples and includes other indications known to those skilled in the art.

6. Methods and Medical Use of the Subject Medicament for Chemotherapeutic Treatment of Conditions Affecting the Circulatory System and Related Organs.

The medicaments disclosed herein are broadly applicable to improved chemotherapeutic treatment of various conditions affecting the circulatory system and related organs of humans and animals. The medicament can be applied, using conventional intracorporeal or topical administration modes, directly or indirectly to, or substantially proximal to, tissues to be treated, including those of the heart, kidneys, liver and blood vessels. Such administration modes provide direct delivery of medicament to, into or substantially proximal to, tissues to be treated, or systemic delivery of medicament to, into or substantially proximal to, tissues to be treated.

Example indications include treatment for: Disease of Cardiac and Pericardial Tissues and Circulatory Tissues, including Arteries and Veins, including Plaques and Infections of such tissues, such as Bacterial Endocarditis; and destruction of unwanted blood vessels, such as spider veins. These examples are provided for illustrative purposes, as the present invention is not limited to the recited examples and includes other indications known to those skilled in the art.

7. Methods and Medical Use of the Subject Medicament for Chemotherapeutic Treatment of Conditions Affecting the Head and Neck.

The medicaments disclosed herein are broadly applicable to improved chemotherapeutic treatment of various conditions affecting the head and neck of humans and animals. The medicament can be applied, using conventional intracorporeal or topical administration modes, directly or indirectly to, or substantially proximal to, tissues to be treated, including those of the head, neck, brain, eyes and ears. Such administration modes provide direct delivery of medicament to, into or substantially proximal to, tissues to be treated, or systemic delivery of medicament to, into or substantially proximal to, tissues to be treated.

Example indications include treatment for: Tumors or Resected Tumor Beds of Intra-cranial and other Head and Neck Tumors; Ophthalmic Tumors and other diseases, including Macular Degeneration and Diabetic Retinopathy; Metastatic Tumors, such as Metastases of Melanoma, Breast or Other Tumors to the Skin of the Head or Neck. These examples are provided for illustrative purposes, as the present invention is not limited to the recited examples and includes other indications known to those skilled in the art.

8. Methods and Medical Use of the Subject Medicament for Chemotherapeutic Treatment of Conditions Affecting the Endocrine and Lymphoreticular Systems and Related Organs.

The medicaments disclosed herein are broadly applicable to improved chemotherapeutic treatment of various conditions affecting the endocrine and lymphoreticular systems and related organs of humans and animals. The medicament can be applied, using conventional intracorporeal or topical administration modes, directly or indirectly to, or substantially proximal to, tissues to be treated, including those of the thyroid gland, the thalamus and hypothalamus, the pituitary gland, lymph nodes and lymphoreticular system. Such administration modes provide direct delivery of medicament to, into or substantially proximal to, tissues to be treated, or systemic delivery of medicament to, into or substantially proximal to, tissues to be treated.

Example indications include treatment for: Hyperplasia, Dysplasia and Neoplasia, Cancer, Inflammation and Infection of the thyroid, Thalamus and Hypothalamus, Pituitary Gland, Lymph Nodes and Lymphoreticular system, including Graves' Disease. These examples are provided for illustrative purposes, as the present invention is not limited to the recited examples and includes other indications known to those skilled in the art.

9. Methods and Medical Use of the Subject Medicament for Chemotherapeutic Treatment of Conditions Affecting Various Other Tissues, such as Connective Tissues and Various Tissue Surfaces Exposed During Surgery.

The medicaments disclosed herein are broadly applicable to improved chemotherapeutic treatment of various conditions affecting various other internal or external tissues of humans and animals, such as connective tissues and various tissue surfaces that become exposed during surgery. The medicament can be applied, using conventional intracorporeal or topical administration modes, directly or indirectly to, or substantially proximal to, tissues to be treated, including those of tissue surfaces exposed during surgery, including endoscopic surgery or other endoscopic procedures. Such application modes provide direct delivery of medicament to, into or substantially proximal to, tissues to be treated, or systemic delivery of medicament to, into or substantially proximal to, tissues to be treated.

Example indications include treatment for: Joint Inflammation, such as that of Arthritis; Resected Tumor Beds of Thoracic, Abdominal, or other Tumors; Metastatic Tumors, such as Metastases of Breast Tumors to the Skin; Tumors or Infections of the Pleura, Peritoneum or Pericardium; and various other substantially similar indications. These examples are provided for illustrative purposes, as the present invention is not limited to the recited examples and includes other indications known to those skilled in the art.

10. Methods and Medical Use of the Subject Medicament for Chemotherapeutic Treatment of Conditions Related to Microbial, Viral Fungal or Parasitic Infection.

The medicaments disclosed herein are broadly applicable to improved chemotherapeutic treatment of various conditions related to microbial, viral, fungal or parasitic infection of humans and animals. The medicament can be applied, using conventional intracorporeal or topical administration modes, directly or indirectly to, or substantially proximal to, tissues to be treated, including those of tissue surfaces exposed during surgery, including endoscopic surgery or other endoscopic procedures. Such administration modes provide direct delivery of medicament to, into or substantially proximal to, tissues to be treated, or systemic delivery of medicament to, into or substantially proximal to, tissues to be treated.

Example indications include treatment for: Bacterial and Antibiotic Resistant Bacterial Infection, including those caused by Gram Positives and Gram Negatives, *Streptomycetes, Actinomycetes, Staphylococci, Streptococci, Pseudomonas, Escherichia coli, Mycobacteria* and others; Infection caused by Filamentous Fungi and Non-filamentous Fungi like *Cryptosporidium, Histoplasma, Aspergillus, Blastomyces, Candida* and others; Parasitic Infection caused by Amoeba (including for use in lysing and killing amoeba in amoebic cysts), *Trichinella, Dirodfilaria* (Heart worm in dogs) and various other substantially similar indications. These examples are provided for illustrative purposes, as the present invention is not limited to the recited examples and includes other indications known to those skilled in the art.

TABLE 1

Physical Properties of Fluorescein and Some Example Halogenated Xanthenes.

| Compound | Substitution | | | | | MW (g) |
|---|---|---|---|---|---|---|
| | X | Y | Z | $R^1$ | $R^2$ | |
| Fluorescein | H | H | H | Na | Na | 376 |
| 4',5'-Dichlorofluorescein | Cl | H | H | Na | Na | 445 |
| 2',7'-Dichlorofluorescein | H | Cl | H | Na | Na | 445 |
| 4,5,6,7-Tetrachlorofluorescein | H | H | Cl | H | H | 470 |
| 2',4',5',7'-Tetrachlorofluorescein | Cl | Cl | H | Na | Na | 514 |
| Dibromofluorescein | Br | H | H | Na | Na | 534 |
| Solvent Red 72 | H | Br | H | H | H | 490 |
| Diiodofluorescein | I | H | H | Na | Na | 628 |
| Eosin B | $NO_2$ | Br | H | Na | Na | 624 |
| Eosin Y | Br | Br | H | Na | Na | 692 |
| Ethyl Eosin | Br | Br | H | $C_2H_5$ | K | 714 |
| Erythrosin B | I | I | H | Na | Na | 880 |
| Phloxine B | Br | Br | Cl | Na | Na | 830 |
| Rose Bengal | I | I | Cl | Na | Na | 1018 |
| 4,5,6,7-Tetrabromoerythrosin | I | I | Br | Na | Na | 1195 |

Table 2. Partition coefficients and toxicology data for several halogenated xanthenes (i.e. Rose Bengal, Erythrosin B and Phloxine B) and selected other therapeutic agents. Partition coefficient, $K_p$, is the ratio of equilibrium concentrations of agent in a lipophilic phase (n-octanol) contacted with an aqueous phase (phosphate buffered saline, PBS, pH=7.4). Toxicology data ($LD_{50}$) for murine intravenous (i.v.) or oral (p.o.) administration.

| Agent | $K_p$ | $LD_{50}$(mg/kg) | |
|---|---|---|---|
| | | i.v. | p.o. |
| Phloxine B | 1.1 | 310 | 310 |
| Erythrosin B | 1.9 | 370 | >1,000 |
| Rose Bengal | 11.5 | | >>1,000 |
| Indocyanine Green | 99 | 60 | |
| Porphyrin HpIX | 1.5 | | >1,000 |

This description has been offered for illustrative purposes only and is not intended to limit the invention of this application.

What is claimed as new and desired to be protected by Letters Patent is set forth in the appended claims.

We claim:

1. An injectable chemotherapeutic pharmaceutical composition consisting of a halogenated xanthene at a concentration of greater than about 0.001% to less than about 20% in aqueous solution, wherein said halogenated xanthene is disodium 4,5,6,7-Tetrabromoerythrosin, and wherein said pharmaceutical composition is for chemotherapeutic treatment of cancer.

2. The pharmaceutical composition of claim 1 wherein said pharmaceutical composition is for the treatment of cancer of the skin, the mouth and digestive tract, the urinary and reproductive tracts, the respiratory tract, the head and neck, and the endocrine and lymphoreticular systems.

3. An injectable chemotherapeutic pharmaceutical composition consisting of a halogenated xanthene in aqueous solution, wherein said halogenated xanthene is disodium 4,5,6,7-Tetrabromoerythrosin, said halogenated xanthene present in a concentration of greater than about 0.001% to less than about 20%, and wherein said pharmaceutical composition is for chemotherapeutic treatment of cancer.

4. An injectable chemotherapeutic pharmaceutical composition consisting of a halogenated xanthene in aqueous solution, wherein said halogenated xanthene is disodium 4,5,6,7-Tetrabromoerythrosin, said halogenated xanthene present in a concentration of about 10%, and wherein said pharmaceutical composition is for chemotherapeutic treatment of cancer.

* * * * *